United States Patent [19]

Abrams

[11] Patent Number: 5,134,890

[45] Date of Patent: Aug. 4, 1992

[54] FLUID FLOW MONITORING DEVICE

[76] Inventor: Lawrence M. Abrams, 133 Huguenot Ave., Englewood, N.J. 07631

[21] Appl. No.: 496,237

[22] Filed: Mar. 20, 1990

[51] Int. Cl.⁵ ............................................. G01F 1/40
[52] U.S. Cl. .................. 73/861.52; 128/725; 73/861.61
[58] Field of Search ................ 73/189, 861.52, 861.61, 73/861.62, 861.63, 861.64; 128/725

[56] References Cited

U.S. PATENT DOCUMENTS

| 1,126,275 | 1/1915 | Rice | 73/861.64 |
|---|---|---|---|
| 1,700,027 | 1/1929 | Connet | 73/861.63 |
| 2,146,371 | 2/1939 | Dunglinson | 73/861.64 |
| 2,197,214 | 4/1940 | Hollander | 73/861.64 |
| 3,147,618 | 9/1969 | Benson | 73/204.21 |
| 3,363,463 | 1/1968 | Wheeler | 73/204.21 |
| 4,688,433 | 8/1987 | Silverwater | 73/861.53 |
| 4,920,808 | 5/1990 | Sommer | 73/189 |

Primary Examiner—Herbert Goldstein
Attorney, Agent, or Firm—Herbert M. Shapiro

[57] ABSTRACT

A flow sensing apparatus has an obstruction extending across the tube to form two openings. The obstruction is at an angle to the tube axis and includes a portion with reduced dimension. Pressure sensors are located on opposite sides of the obstruction.

6 Claims, 3 Drawing Sheets

FLUID FLOW MONITORING DEVICE

FIELD OF THE INVENTION

This invention relates to patient gas flow monitoring devices and more particularly to Pneumotachographs, Pneumotachometers, or Anemometers, referred to herein as Pneumotachs particularly adapted for patient end use.

BACKGROUND OF THE INVENTION

Human beings are capable of a wide variety of gas flow rates of from, for example, 0.1 liter per second to 16 liters per second. Moreover, many medical studies require that small changes in lung function be measured accurately and reproducible over time.

Another characteristic of gas flow which has medical significance is the rate at which gas flow changes. Flow that changes rapidly is described as having a high frequency constant. If a medical ventilator is attached to a patient, it may superimpose relatively high frequencies during inspiration. The ability of a gasflow measuring device to measure high frequency changes in flow rate is described as the "frequency response" of the device.

A Rotometer is another type of flow meter designed to measure steady, unchanging Oxygen flow. But these devices have too much inertia to respond quickly to rapid change in flow. Rotometers, thus have a low frequency response and would not make good Pneumotachs, for example, for diagnostic spirometry. Rotometers would respond inadequately at high flow rates and report lower than actual peak rates. Any Pneumotachs with high inertia do not respond quickly enough to rapidly changing flow rates. Accordingly, Pneumotachs may overstate or understate the airflow rates during, for example, a forced vital capacity (FVC) maneuver.

Another requirement for accurate airflow measurement is that the airflow measuring device should not impede the patients breathing ability. Consequently, the device should not have a high resistance to airflow. A reasonable maximum back pressure which a patient should encounter with such a device is 1.5 cm water per liter per second air flow.

Other requirements for flow rate measuring devices are that dead space volume of the device should be less than 5.0 milliliters for nonatal monitoring and less than 15 milliliters for adult monitoring.

One major problem with the use of Pneumotachs for ventilation monitoring is moisture and patient secretions which may render the device inoperative.

Prior art Pneumotachs fail to meet these various requirements. A typical Pneumotach is characterized by a bundle of capillary tubes which provide a small fixed resistance to gas flow. Flush openings (air taps) at both ends of the capillary tubes are used to measure the pressure difference created when gas flows through the device. The resulting pressure difference is very low, usually less than two centimeters of water. An electronic pressure transducer is used to measure the rapid changes in pressure when gasflow changes rapidly.

The capillary tubes usually are made of brass and the case is made of stainless steel. Different sizes are used for the capillaries to cover different flow ranges. Some Pneumotachs include capillaries formed in extruded ceramic material. The ceramic tends to absorb moisture thus avoiding tube occlusion to some extent. But such devices are large usually requiring sufficient length of tubing to produce laminar flow. This reduces portability and increases dead space.

Other types of Pneumotachs utilize fine mesh screens rather than capillaries. The screen Pneumotachs exhibit decreased dead space, slightly better frequency response, and easier disassembly for cleaning. Pneumotachs with three screens are also available. The center screen acts as a resistance element; the other two act to smooth the flow of gas. The screens also may be heated to reduce water condensation without heating the gasflow through them.

But screens clog easily and need frequent cleaning. They have been protected by filters which are disposable. But, the use of filters is limited by the fact that filters increase resistance and expense.

Large orifice Pneumotachs have been developed to permit passage of water droplets. But turbulent gasflow results requiring more sophisticated electronics to linearize the output. "Variable Orifice" Pneumotachs were developed to linearize the output mechanically.

Hot wire and turbine Pneumotachs have been developed for measuring airflow by its cooling properties and by the rate of rotation of turbine blades, respectively. The first of these have not proven to be very accurate for gasflow measurement because they become affected by moisture and non laminar flow. The second is affected by fluid composition, is unidirectional, and is limited in its frequency response by its inertia and momentum.

Similarly, Vortex Pneumotachs are inaccurate at low flow rates because they require fully developed turbulent flow which is achieved only above a certain flow velocity. Also, a long upstream straight section is required to prevent uneven flow patterns. Ultrasonic Pneumotachs have been developed to count vortices generated in the airflow and the speed of ultrasonic waves travelling through the tube. But they are expensive and very sensitive to change in density and temperature.

Although considerable development effort has gone into Pneumotach design, no ideal Pneumotach has become available. Those that are available are limited in range, are expensive, need extensive care and frequent calibration.

BRIEF DESCRIPTION OF AN EMBODIMENT OF THIS INVENTION

In accordance with the principles of the present invention, a gas flow monitoring and control system includes a Venturi tube which is useful over a wide range of flow rates required for common medical usage. Moreover, the system is relatively inexpensive, virtually eliminates dead space, and is characterized by a broad frequency response. Although Venturi tubes are in common use for measuring fluid flow, they are not useful for measuring gas flow primarily because of the fact that they exhibit a pure square wave characteristic (differential pressure as a function of increasing flow) whereas a linear characteristic is necessary for gas flow measurement. The square wave characteristic means that the entire effective range of a given transducer would correspond to a narrow flow range. Thus, the use of such an instrument would be considered limited at best. Further, air flow measurement requires tiny restrictions leading to a minimal pressure drop and a very sensitive pressure transducer. These considerations are not easily satisfied with a Venturi tube except such tubes of the critical flow variety which are not useful for patient airflow monitoring.

The present invention is based on the recognition that a Venturi tube can be used as a Pneumotach to measure gas flow if it is designed for the measurement of compressible gases in an operating range in which those gases are incompressible and act as a fluid.

A Venturi tube also is a unidirectional device. In accordance with the principles of the present invention, a bidirectional Venturi tube is provided. It is believed that the use of a Venturi tube for gas flow monitoring and control as well as bidirectional Venturi tubes represent a significant departure from prior art thinking.

DETAILED DESCRIPTION OF ILLUSTRATIVE EMBODIMENTS OF THIS INVENTION

Figure 1:
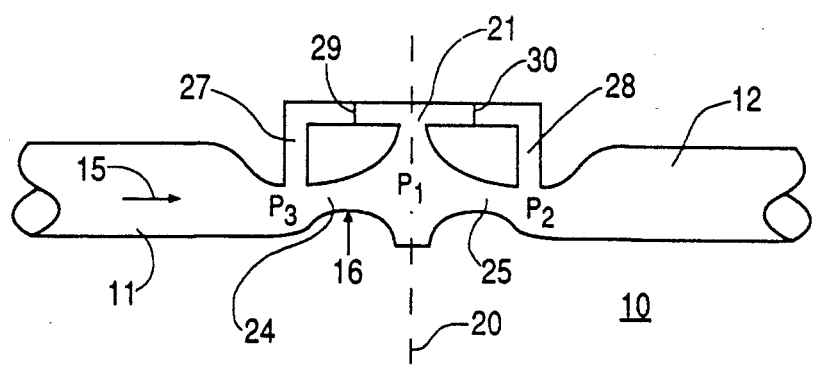
FIG. 1 is a schematic cross sectional view of a Venturi tube Pneumotach in accordance with the principles of this invention.

FIG. 1 shows a bidirectional Venturi tube 10 useful in accordance with the principles of this invention. The tube includes an inlet 11 and an outlet 12 for gas flowing from left to right as viewed and as indicated by arrow 15.

Tube 10 also includes a flow constriction region 16 where the diameter of the tube is reduced. A Venturi tube derives its characteristic from such a constriction. The constriction provides a pressure differential which is a function of the constriction dimensions and the flow rate of the gas through the tube. The tube can be seen to be symmetrical about an axis of symmetry represented by broken line 20. A gas tap 21 is located at the axis of symmetry where the diameter of the tube enlarges to the right to define a second gas flow constriction 25.

A gas tap is provided for each constricted area 16 and 25 as shown by taps 27 and 28. Taps 27 and 28 are separated from tap 21 by diaphragms 29 and 30, respectively. For flow as viewed from left to right, taps 21 and 28 are operative producing a differential pressure on either side of diaphragm 30. Tap 21 senses pressure $p_1$, the upstream pressure, which is greater than the pressure $p_2$, sensed by tap 28. Pressure $p_2$ is the downstream pressure produced by flow through constriction 25. Because the Venturi tube is symmetrical, outlet 12 may be used as the inlet to the tube in which case "inlet" 11 becomes the outlet and gas flow is in a direction opposite to that indicated by arrow 15. For air flow from right to left, as viewed, pressure ($p_1$) at tap 21 is greater than pressure ($p_3$) at tap 27. As is clear from the description, the Venturi tube of FIG. 1 is entirely symmetrical.

The use of a common pressure ($p_1$) against two separate diaphragms and pressures ($p_2$ and $p_3$) allows direction to be sensed. If flow is from left to right, simultaneous measurement of $p_2-p_1$ and $p_3-p_1$, allows determination of direction since $(p_2-p_1)(p_3-p_1)=p_2=p_3$ which identifies direction by its sign.

The Venturi tube of FIG. 1 may be connected directly into an air duct coupled to the mouth of a patient. Because the tube is bidirectional, the airflow can be measured when the patient inhales or exhales.

Figure 2:
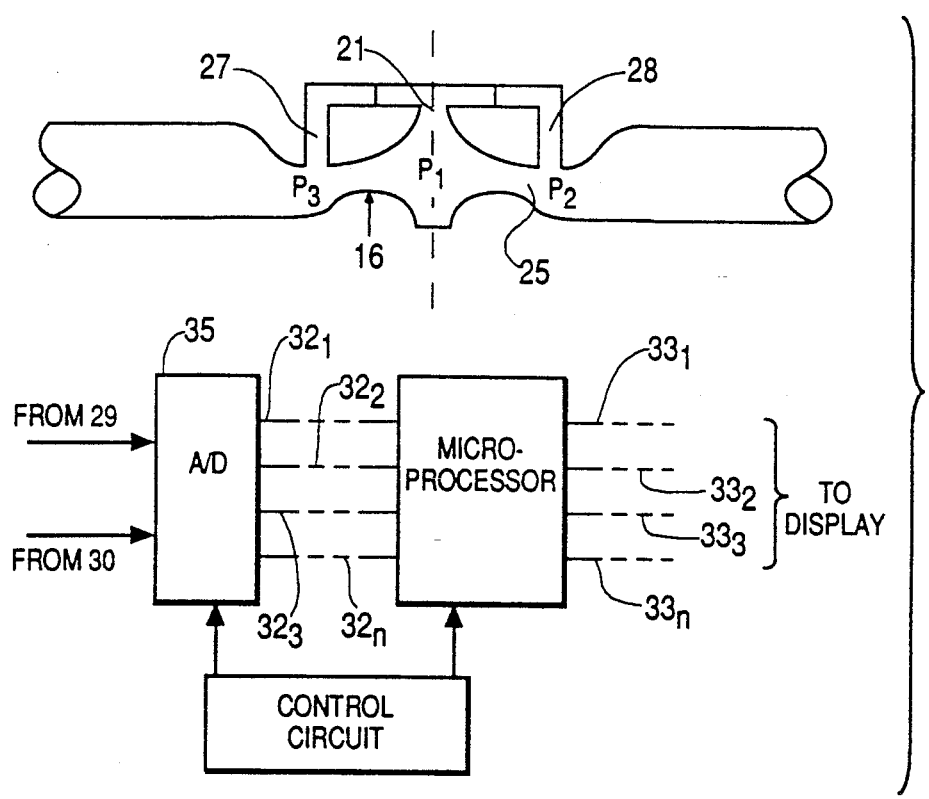
FIG. 2 is a schematic block diagram of a circuit for obtaining a linearized output from the Pneumotach of FIG. 1.

FIG. 2 shows a circuit useful for indicating airflow rate and direction. The circuit is responsive to slight deflections of diaphragm 29 or 30 to indicate flow rate and direction. The circuit comprises microprocessor 31 having inputs $32_1$, $32_2$, $32_3$, - - - $32_m$ and outputs $33_1$, $33_2$, $33_3$, - - - $33_m$. Diaphragms 29 and 30 may comprise, for example, piezoelectric devices which are responsive to pressure changes to produce an electric current due to the Neel effect. That electric current is applied to inputs to an analog to digital (A/D) converter 35. The outputs from the converter are connected to inputs to the microprocessor for applying to it digital codes representative of pressure differences $p_2-p_1$ or $p_3-p_1$ and indicative of airflow direction. The outputs from the microprocessor are applied to a suitable display not shown.

The direction of current flow in a piezoelectric film is indicative of deflection of the film. The direction of deflection is determined by the direction of the pressure differential. Also, the magnitude of the current is a measure of the magnitude and rate of change of the pressure differential. Thus, the current direction and magnitude in diaphragm 29 or 30 represents the flow rate of the gas from left to right or right to left, respectively, as viewed in FIG. 1. A suitable sensor using a Piezoelectric film is available from Penwalt Corporation of King Of Prussia, PA.

Figure 3:
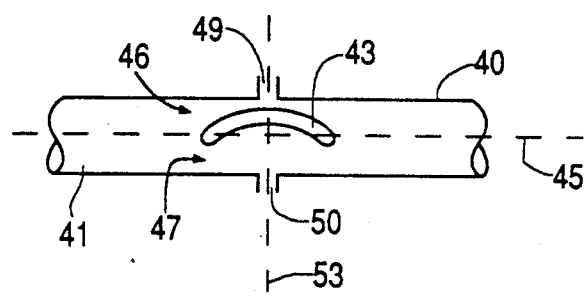
FIGS. 3 through 8 are schematic cross sectional views of alternative Venturi Pneumotachs in accordance with the principles of this invention.

FIG. 3 shows an alternative embodiment to that shown in FIG. 1. The Venturi tube in this instance has a constant diameter as indicated by lines 40 and 41 in the figure representing the top and bottom edges of the tube. The requisite gas flow constriction is provided by an airfoil or wing structure 43. Airfoil 43 extends across the tube and is rigid for the gas flow rates contemplated.

The airfoil can be seen to have its long, dimension parallel to the axis 45 of the Venturi tube. The airfoil is curved to provide a narrow passageway 46 for gas flow above it and a wider passageway 47 below it, as viewed. Taps 49 and 50 correspond to taps 27 and 21 or 28 and 21 of FIG. 1, respectively, the pressure in passageway 46 being relatively lower than the pressure in passageway 47 for gas flowing from left to right or from right to left, as viewed. The Venturi tube of FIG. 3 can be seen to be symmetrical about axis of symmetry 53.

Figure 4:
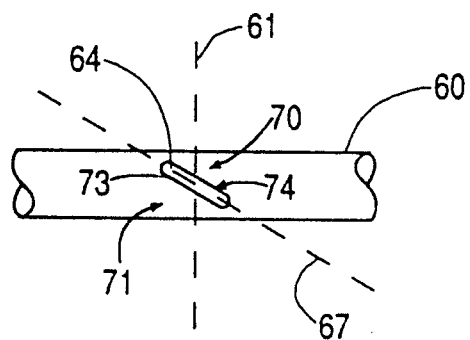

FIG. 4 shows an alternative Venturi tube 60 having an axis of symmetry 61. The tube can be seen to have a constant diameter with the requisite gas flow constriction being provided by airfoil 64. The airfoil, in this instance, is itself symmetrical along an axis 67 at an angle to the axis of symmetry 61. The airflow defines first and second passageways 70 and 71 of restricted cross sections thus defining the constrictions characteristic of Venturi tubes.

Passageways 70 and 71 have like cross sections. The requisite pressure differential is achieved by the angle that the axis of symmetry 67 makes with the axis of symmetry 61. Piezoelectric sensors 73 and 74 are positioned, as shown, to either side of the airfoil near or at the center line of tube 60 for measuring that pressure differential in a manner analogous to that described in connection with FIG. 1. No taps for measuring static pressure are needed in this embodiment because the pressure sensing transducers (73 and 74) are placed directly in the main gas stream.

Figure 5:
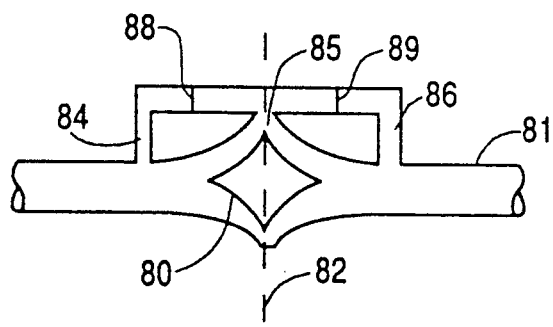

FIG. 5 shows an embodiment where an airfoil 80 is employed but where the Venturi tube 81 itself is also contoured to define the requisite constriction. The airfoil, illustratively, has a diamond cross section aligned with the axis of symmetry 82. The tube includes taps 84, 85, and 86, tap 85 being aligned with the axis of symmetry. Diaphragms 88 and 89 are operative as are diaphragms 29 and 30 of FIG. 1.

The cross sectional area of the space defined by the annular oriface created by the tube and the center foil can be larger or smaller than the cross sectional area of the entrance or exit tubes at taps 84 and 86. If the cross sectional area along axis 82 is smaller than that at the parallel axis through 84 and 86, then tap 85 measures the Venturi pressure for the upstream tap 84 when the flow is left to right. Likewise, when flow is from right to left, tap 86 registers upstream pressure while tap 85 measures throat pressure. However, if the cross sectional area of the annular oriface through axis 82 is larger than that through the parallel axis through 84 and 86, then the embodiments of FIG. 5 functions more like that of FIG. 1 where the pressure at tap 85 is always the upstream pressure for the corresponding downstream pressure measured at 86 (left to right) or 84 (right to left). The principle difference in this case between the embodiments of FIGS. 1 and 5 is the presence of the center foil to control flow (less turbulence).

Figure 6:
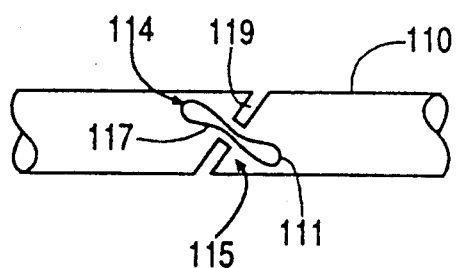

FIG. 6 shows a Venturi tube 110 which also employs an airfoil 111 to define first and second passageways 114 and 115 for gas. In this instance, passageway 114 has a cross sectional area identical to that of passageway 115. The distinguishing feature of the embodiment of FIG. 6 is that the area 117 of the airfoil is made thin to function as a diaphragm. A pressure transducer such as a magnetic inductive sensor is inserted into small diameter shaft 119 and is magnetically coupled to the diaphragm for detecting pressure differentials caused by the deflection of the diaphragm due to gas flow. Shaft 119 is the equivalent of a tubular channel crossing the center axis of tube 110 and only negligibly impedes fluid flow in the tube. A suitable sensor is available commercially from Keyence corporation, Fairlawn N.J. In this embodiment, the sensed element is isolated from the sensor head. Thus, fluid and gas isolation as well as contamination protection is provided.

Figure 7:
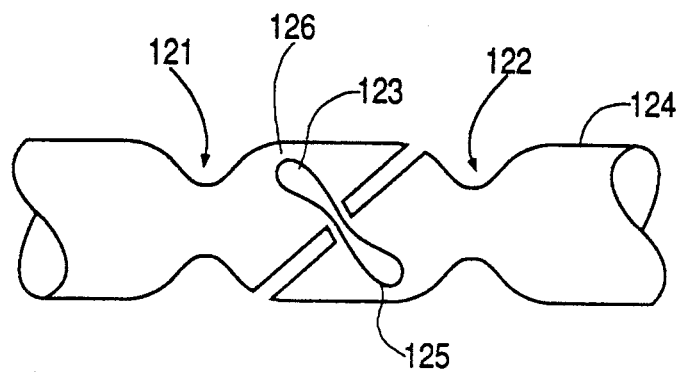

FIG. 7 shows an embodiment similar to that shown in FIG. 6. But in this embodiment, the Venturi tube 124 has areas 121 and 122 of reduced diameter to either side of air foil 123. The areas 121 and 122 are provided for the purpose of directing air flow to the appropriate side of the foil, channel 125 and 126, respectively, regardless of the gas inlet profile.

Figure 8:
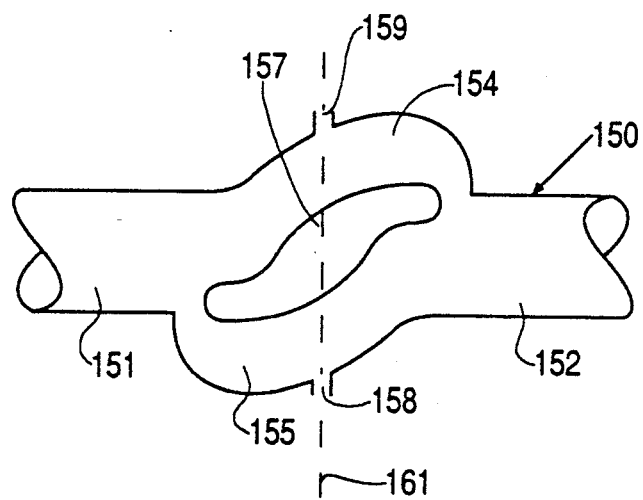

FIG. 8 shows an embodiment similar to that of FIG. 7 except that the entire inlet and outlet passageways are of reduced diameter. Specifically, the tube 150 of FIG. 8 includes passageways 151 and 152 oriented to direct airflow through channels 154 and 155, respectively, which are defined by airfoil 157. Taps 158 and 159 provide access to the respective channels for, for example, disposable Silicon type transducers and diaphragms. Such transducers are available commercially from Honeywell Corporation, Minneapolis Minn. and are suitable also for embodiments of the type shown in FIG. 7.

In one prototype of the embodiment of FIG. 8, taps 158 and 159 are provided in alignment with a vertical axis 161 through the center of airfoil 157. The passageways 154 and 155 are 0.060 inch defining a 0.028 square inch opening. The length of the airfoil is one inch, has a maximum thickness of 0.125 inch and end portions defined by a circle with a 0.62 inch radius. The inlet openings are 0.375 inch defining a 0.110 square inch area. The overall length of the prototype is four inches.

The prototype is injection molded and is expected to cost on the order of ten cents in mass production. It is made of plastic and is not affected by mucous or moisture. The device is operative over a wide range of flow rates of from 0.1 liters per second to 20 liters per second and exhibits a high degree of pressure sensitivity (to thousands of an inch of water) over the entire range. The frequency range of the device is greater than the sensitivity of commercially available high frequency Silicon transducers. Hydrophilic plastics can be used to allow removal of any water accumulation in the device.

The transducer is expected to cost on the order of a few dollars in quantity and so the entire device is disposable. Thus, a disposable Venturi Pneumatach is provided which overcomes virtually all the problems encountered by prior art devices and is dimensioned to maintain gas in an incompressible range over the range of operation required for patient end use.

Venturi tubes are available in a "critical flow" configuration which is designed for a specific pressure at the constriction and requires no tap there. Another type of Venturi tube requires a tap at the constriction. Critical flow tubes can be made with very small dimensions but are not suited for flow sensing where flow is dynamic, sometimes stopping and sometimes reversing. The later tubes are limited to larger than 3 inch diameter openings. Also, pressure drop across the tube (head loss) is very large for the latter type of tubes, far greater than is permissable for patient usage. But by molding smooth internal surfaces and transitions, head loss can be reduced to a range compatable with patient end use.

The invention relates generally to Venturi tubes of the non critical flow configuration useful for patient end use and to bidirectional Venturi tubes of both critical flow and non critical flow configuration.

The invention has been described in terms of gas flow monitoring primarily. But apparatus suitable for liquid flow monitoring also may be devised according to the principles of this invention. Thus, air foil 43 of FIG. 3 may be a hydrafoil (or fluid foil) for liquid flow monitoring.

Further, it was stated above in connection with the description of FIG. 1 that the apparatus may be connected directly to an air duct coupled to the mouth of a patient. There is no need for a long length of tubing to provide laminar flow for the upstream port. Constriction 16 of FIG. 1 controls the flow and the nature of the flow in the supply tube has no effect on the pressure read at tap 21.

What is claimed is:

1. Fluid flow sensing apparatus comprising a tube having a first axis and first and second open ends for introducing fluids, said tube including an obstruction to fluid flow, said obstruction extending across the width of said tube and defining first and second openings for fluid passage to first and second sides thereof, said openings having areas smaller than that of said tube for defining constrictions to fluid flow in said tube, said obstruction being positioned at an angle to said first axis and having a cross section with at least a first portion thereof of reduced dimensions, said apparatus including first and second pressure sensing means to first and second sides of said obstruction for providing an indication of the rate of flow to both sides of said obstruction.

2. Apparatus as set forth in claim 1 wherein said apparatus includes first and second large surfaces to first and second sides thereof wherein said first and second pressure sensing means are located at said first and second large surfaces respectively.

3. Apparatus as set forth in claim 2 wherein said first and second pressure sensing transducers comprise piezoelectric devices.

4. Apparatus as set forth in claim 1 also including first and second taps to said first and second openings respectively and pressure sensing means for measuring pressure differentials between the pressures at said first and second taps.

5. Apparatus as set forth in claim 1 wherein said obstruction divides said tube into first and second paths wherein each of said first and second paths includes at least a center portion thereof having a reduced cross section for directing the flow of fluid to first and second sides of said obstruction.

6. Apparatus as set forth in claim 1 wherein said obstruction includes a section of reduced thickness and a diaphragm positioned at said section, said apparatus also including means for sensing pressure differentials caused by the deflection of said diaphragm due to fluid flow.

* * * * *